(12) United States Patent
Yamashita et al.

(10) Patent No.: US 10,815,504 B2
(45) Date of Patent: Oct. 27, 2020

(54) METHOD FOR PRODUCING (Z)-2-BENZOYLOXY-12-HEPTADECENE AND (2S,12Z)-2-HYDROXY-12-HEPTADECENE AND METHOD FOR PRODUCING (2S,12Z)-2-ACETOXY-12-HEPTADECENE

(71) Applicant: Shin-Etsu Chemical Co., Ltd., Tokyo (JP)

(72) Inventors: Miyoshi Yamashita, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 16/107,349

(22) Filed: Aug. 21, 2018

(65) Prior Publication Data

US 2018/0355386 A1 Dec. 13, 2018

Related U.S. Application Data

(62) Division of application No. 14/837,683, filed on Aug. 27, 2015, now Pat. No. 10,081,820.

(30) Foreign Application Priority Data

Sep. 16, 2014 (JP) ................. 2014-187596

(51) Int. Cl.
| | | |
|---|---|---|
| *C12P 7/62* | (2006.01) | |
| *C07C 29/09* | (2006.01) | |
| *C07C 303/28* | (2006.01) | |
| *C07C 309/66* | (2006.01) | |
| *C07C 33/025* | (2006.01) | |
| *C07C 67/08* | (2006.01) | |
| *C07C 69/145* | (2006.01) | |
| *C07C 69/78* | (2006.01) | |
| *C07C 29/80* | (2006.01) | |
| *C07C 67/10* | (2006.01) | |
| *C07C 67/54* | (2006.01) | |

(52) U.S. Cl.
CPC .............. *C12P 7/62* (2013.01); *C07C 29/095* (2013.01); *C07C 29/80* (2013.01); *C07C 67/08* (2013.01); *C07C 67/10* (2013.01); *C07C 67/54* (2013.01); *C07C 69/78* (2013.01); *C07C 303/28* (2013.01); *C07B 2200/07* (2013.01); *C07B 2200/09* (2013.01)

(58) Field of Classification Search
CPC . C12P 7/62; C07C 69/78; C07C 67/08; C07C 303/28; C07C 69/145; C07C 67/10; C07C 67/54; C07C 29/095; C07C 309/66; C07C 309/73; C07C 33/025; C07C 29/80; C07B 2200/07; C07B 2200/09
USPC ........................................................ 560/113
See application file for complete search history.

(56) References Cited

FOREIGN PATENT DOCUMENTS

| WO | 2002055724 | 7/2002 |
|---|---|---|
| WO | 2007079563 | 7/2007 |

(Continued)

OTHER PUBLICATIONS

Turcu MC. Lipase-cataLyzed approaches towards secondary alcohols: intermediates for enantiopure drugs. University of Turku, Turku 2010. Thesis, Annales Universitatis Turkuensis, Painosalama Oy, Turku, Finland 2010, ISBN 978-951-29-4346-3, p. 1-73. (Year: 2010).*

European Search Report corresponding to European Application No. 15182476.0 (dated Jan. 7, 2016).

Gries et al. "(2S,12Z)-2-Acetoxy-12-heptadecene: Major Sex Pheromone Component of Pistachio Twig Borer, *Kermania pistaciella*" Journal of Chemical Ecology, 32:2667-2677 (2006).

(Continued)

*Primary Examiner* — Yih-Horng Shiao
(74) *Attorney, Agent, or Firm* — Myers Bigel, P.A.

(57) ABSTRACT

Provided are methods including a method for industrially producing (2S,12Z)-2-acetoxy-12-heptadecene, which is, for example, a sex pheromone of pistachio twig borer. The methods can include a production method comprising a step of reacting racemic (2RS,12Z)-2-hydroxy-12-heptadecene with vinyl benzoate in the presence of a lipase to obtain a mixture of optically active (2R,12Z)-2-benzoyloxy-12-heptadecene of Formula (R,Z-2) and optically active (2S,12Z)-2-hydroxy-12-heptadecene of Formula (S,Z-1), a step of heating the mixture to distill out the optically active (2S,12Z)-2-hydroxy-12-heptadecene (S,Z-1), and a step of acetylating the optically active (2S,12Z)-2-hydroxy-12-heptadecene (S,Z-1) to obtain optically active (2S,12Z)-2-acetoxy-12-heptadecene of Formula (S,Z-3).

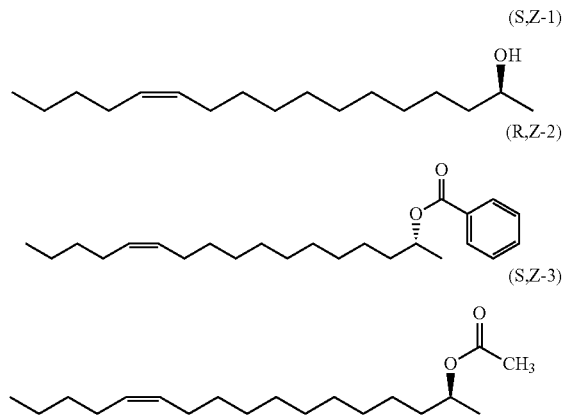

3 Claims, No Drawings

(56) References Cited

FOREIGN PATENT DOCUMENTS

| WO | WO 2007/079563 | * | 7/2007 |
| WO | 2007118297 | | 10/2007 |

OTHER PUBLICATIONS

Turcu, Mihaela Claudia "Lipase-Catalyzed Approaches Towards Secondary Alcohols: Intermediates for Enantiopure Drugs" Annales Universitatis Turkuensis, Painosalama Oy, Turku, Finland (pp. 1-73) (2010).

Vosmann et al. "Preparation of lipophilic alkyl (hydroxyl)benzoates by solvent-free lipase-catalyzed esterification and transesterification" Applied Microbiology and Biotechnology, 80:29-36 (2008).

* cited by examiner

METHOD FOR PRODUCING (Z)-2-BENZOYLOXY-12-HEPTADECENE AND (2S,12Z)-2-HYDROXY-12-HEPTADECENE AND METHOD FOR PRODUCING (2S,12Z)-2-ACETOXY-12-HEPTADECENE

RELATED APPLICATIONS

This application is a divisional of U.S. patent application Ser. No. 14/837,683, filed Aug. 27, 2015, which claims priority from Japanese Patent Application No. 2014-187596, filed Sep. 16, 2014, the disclosure of each of which is incorporated by reference herein in its entirety.

FIELD AND BACKGROUND OF THE INVENTION

The present invention relates to methods for producing (Z)-2-benzoyloxy-12-heptadecene and optically active (2S, 12Z)-2-hydroxy-12-heptadecene, and a method for producing optically active (2S,12Z)-2-acetoxy-12-heptadecene, which is, for example, a pheromone component of pistachio twig borer that is a major insect pest of pistachio trees.

Pistachio twig borer (scientific name: *Kermania pistaciella*) is a significant insect pest of pistachio trees in Iran, Turkey and the like. Larvae of the insect damage pistachio trunks and cause serious problems such as reductions in crop yield and crop quality. At the present time, insecticides are used to control the pistachio twig borer but achieve an insufficient effect and may cause environmental and human health concerns. In such circumstances, there is a demand for the development of novel insect pest control techniques such as mating disruption and mass trapping by using a sex pheromone of the insect.

As a sex pheromone of the pistachio twig borer, R. Gries et al. reported optically active (2S,12Z)-2-acetoxy-12-heptadecene in 2006 (see WO 2007/079563 (Turkish Patent Application Publication No. 200805195) and R. Gries et al., J. Chem. Ecol., (2006) 32: 2667). It is also found that (2R,12Z)-2-acetoxy-12-heptadecene, the stereoisomer of the above compound, exhibits an attraction-inhibiting effect (see WO 2007/079563 (Turkish Patent Application Publication No. 200805195) and R. Gries et al., J. Chem. Ecol., (2006) 32: 2667).

R. Gries et al. also disclose methods for producing (2S,12Z)-2-acetoxy-12-heptadecene, the sex pheromone of the pistachio twig borer. In one method, optical resolution is used in which racemic (2RS,12Z)-2-hydroxy-12-heptadecene is reacted with vinyl acetate in the presence of a lipase as an esterase to obtain (2S,12Z)-2-hydroxy-12-heptadecene, and the obtained (2S,12Z)-2-hydroxy-12-heptadecene is acetylated; and in the other method, optically active (S)-propylene oxide is used (see WO 2007/079563 (Turkish Patent Application Publication No. 200805195) and R. Gries et al., J. Chem. Ecol., (2006) 32: 2667).

SUMMARY OF THE INVENTION

However, in one of the production methods previously reported by R. Gries et al., silica gel column chromatography is required for the separation between (2S,12Z)-2-hydroxy-12-heptadecene and (2R,12Z)-2-acetoxy-12-heptadecene produced by acetylation in the presence of an enzyme catalyst. In the other method in which optically active (S)-propylene oxide is used, the (S)-propylene oxide is expensive and thus is not easily available on an industrial scale. On this account, these methods have various problems as the industrial mass production methods.

In view of the above circumstances, the present invention has been made to solve the problems of the conventional production methods. An object of the present invention is to provide a method for industrially producing (2S,12Z)-2-acetoxy-12-heptadecene, which is, for example, the sex pheromone of pistachio twig borer.

The inventors of the present invention have found that a mixture of optically active (2R,12Z)-2-benzoyloxy-12-heptadecene and optically active (2S,12Z)-2-hydroxy-12-heptadecene is produced from racemic (2RS,12Z)-2-hydroxy-12-heptadecene, and each compound in the mixture can be easily separated with a simple distillation apparatus; and have completed the present invention.

In an aspect of the present invention, there can be provided a method for producing optically active (2R,12Z)-2-benzoyloxy-12-heptadecene, comprising the steps of:

reacting racemic (2RS,12Z)-2-hydroxy-12-heptadecene with vinyl benzoate in the presence of a lipase as an esterase to obtain a mixture of optically active (2R,12Z)-2-benzoyloxy-12-heptadecene represented by Formula (R,Z-2):

(R,Z-2)

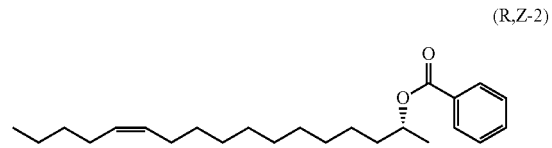 [SMILES: CCCC/C=C\CCCCCCCCC[C@@H](C)OC(=O)c1ccccc1]

and optically active (2S,12Z)-2-hydroxy-12-heptadecene represented by Formula (S,Z-1):

(S,Z-1)

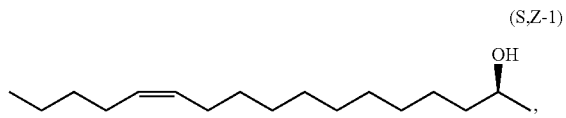 [SMILES: CCCC/C=C\CCCCCCCCC[C@H](C)O]

and heating the mixture for distilling off the optically active (2S,12Z)-2-hydroxy-12-heptadecene (S,Z-1) to obtain the optically active (2R,12Z)-2-benzoyloxy-12-heptadecene (R,Z-2) as a residue.

In a further aspect of the invention, there can be provided a method for producing optically active (2S,12Z)-2-acetoxy-12-heptadecene, the method comprising:

the steps comprised by the method for producing optically active (2R,12Z)-2-benzoyloxy-12-heptadecene;

a step of hydrolyzing the produced optically active (2R,12Z)-2-benzoyloxy-12-heptadecene to obtain (2R,12Z)-2-hydroxy-12-heptadecene; and a step of subjecting a hydroxy group of the (2R,12Z)-2-hydroxy-12-heptadecene to mesylation (methanesulfonylation) or tosylation (p-toluenesulfonylation) followed by acetoxylation to obtain the optically active (2S,12Z)-2-acetoxy-12-heptadecene represented by Formula (S,Z-3):

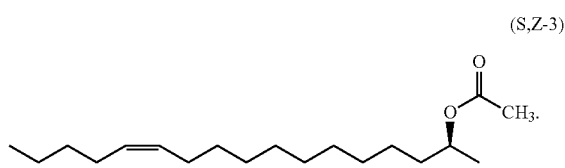 [SMILES: CCCC/C=C\CCCCCCCCC[C@H](C)OC(C)=O]

In an aspect of the present invention, there can be provided a method for producing optically active (2S,12Z)-2-hydroxy-12-heptadecene, comprising the steps of:

reacting racemic (2RS,12Z)-2-hydroxy-12-heptadecene with vinyl benzoate in the presence of a lipase as an esterase to obtain a mixture of optically active (2R,12Z)-2-benzoyloxy-12-heptadecene represented by Formula (R,Z-2) and optically active (2S,12Z)-2-hydroxy-12-heptadecene represented by Formula (S,Z-1), and heating the mixture to distill out the optically active (2S,12Z)-2-hydroxy-12-heptadecene (S,Z-1).

In a further aspect of the present invention, there can be provided a method for producing optically active (2S,12Z)-2-acetoxy-12-heptadecene, comprising:

the steps comprised by the method for producing optically active (2S,12Z)-2-hydroxy-12-heptadecene, and a step of acetylating the produced optically active (2S,12Z)-2-hydroxy-12-heptadecene to obtain optically active (2S,12Z)-2-acetoxy-12-heptadecene represented by Formula (S,Z-3):

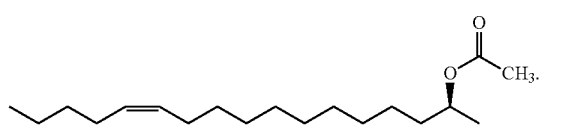

In an aspect of the present invention, there can be provided (Z)-2-benzoyloxy-12-heptadecene represented by Formula (RS,Z-2):

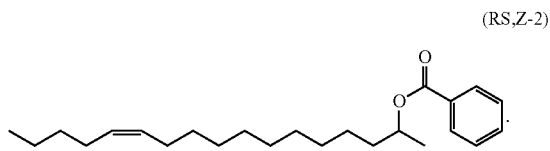 [SMILES: CCCC/C=C\CCCCCCCCCC(C)OC(=O)c1ccccc1]

According to the present invention, (2S,12Z)-2-acetoxy-12-heptadecene, which is, for example, the sex pheromone of pistachio twig borer, can be produced efficiently on an industrial-scale with a simple apparatus.

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

A mixture of optically active (2R,12Z)-2-benzoyloxy-12-heptadecene represented by Formula (R,Z-2) and optically active (2S,12Z)-2-hydroxy-12-heptadecene represented by Formula (S,Z-1) can be produced by reacting racemic (2RS,12Z)-2-hydroxy-12-heptadecene represented by Formula (RS,Z-1) with vinyl benzoate in an organic solvent in the presence of a lipase as an esterase, thereby benzoylating the (2R,12Z)-2-hydroxy-12-heptadecene.

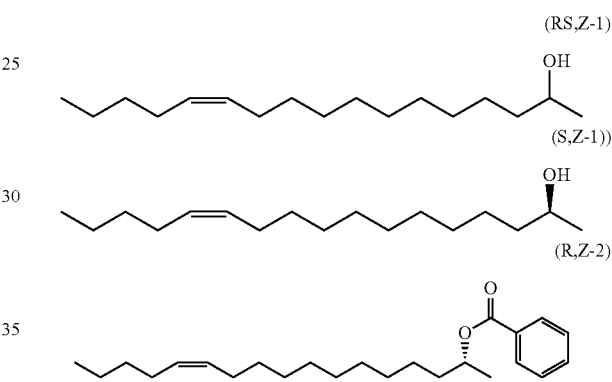

The racemic (2RS,12Z)-2-hydroxy-12-heptadecene (RS,Z-1) can be produced by a known method, for example, the method described in WO 2007/079563 (Turkish Patent Application Publication No. 200805195) and R. Gries et al., J. Chem. Ecol., (2006) 32: 2667. More specifically, (Z)-11-hexadecenal can be reacted with a methyl magnesium halide in an ether solvent such as tetrahydrofuran or diethyl ether to produce the racemic (2RS,12Z)-2-hydroxy-12-heptadecene.

The lipase as an esterase may be any lipase exhibiting the catalytic activity of specifically benzoylating the (2R,12Z)-2-hydroxy-12-heptadecene in racemic (2RS,12Z)-2-hydroxy-12-heptadecene (RS,Z-1). Examples of the lipase include lipases produced by microorganisms belonging to at least one genus selected from *Aspergillus, Candida, Pseudomonas, Mucor* and others. Examples of the microorganism belonging to *Aspergillus* include *Aspergillus niger*. Examples of the microorganism belonging to *Candida* include *Candida Antarctica*. Examples of the microorganism belonging to *Pseudomonas* include *Pseudomonas fluorescens*. In particular, a lipase derived from *Candida antarctica* is preferred from the standpoint of reactivity. The lipase may be in the form of microorganisms, bacterial cells, an enzyme, or an immobilized enzyme prepared by immobilizing the enzyme to an insoluble carrier such as a synthetic resin or a mineral. From the standpoint of stability, the immobilized enzyme prepared by immobilization to an insoluble carrier is preferred. Examples of a preferred commercial product include Novozym435 (enzyme unit: 1,000 unit/g, manufactured by Novozymes) produced by supporting the lipase derived from *Candida antarctica* on an acrylic resin.

The amount of the lipase to be used is, in terms of unit (U) indicating enzyme activity, preferably from 5,000 units to 50,000 units; and from the standpoint of reaction rate and the deactivation of enzyme catalyst, particularly preferably from 10,000 units to 30,000 units.

The organic solvent used for the benzoylation may be any solvent which does not adversely affect the reaction. Examples of the solvent include hydrocarbons such as hexane, benzene and toluene; ethers such as tetrahydrofuran, 1,4-dioxane, diethyl ether, diisopropyl ether and t-butyl methyl ether; ketones such as acetone, methyl ethyl ketone, cyclohexanone and 4-methyl-2-pentanone; and esters such as methyl acetate, ethyl acetate and butyl acetate. From the standpoint of enzyme catalyst activity and stability, preferred are hydrocarbons such as hexane, benzene and toluene; and ethers such as tetrahydrofuran, 1,4-dioxane, diethyl ether, diisopropyl ether and t-butyl methyl ether. Particularly preferred are hexane, toluene, tetrahydrofuran, diisopropyl ether and t-butyl methyl ether.

The amount of the organic solvent used for the benzoylation is preferably from 500 ml to 1,200 ml, and from the standpoint of enzyme catalyst stability and reaction rate, particularly preferably from 700 ml to 1,000 ml, relative to 1 mol of racemic (2RS,12Z)-2-hydroxy-12-heptadecene.

The amount of the vinyl benzoate to be used is preferably from 0.5 equivalents to 1.0 equivalent, and from the standpoint of reactivity and cost efficiency, particularly preferably from 0.6 equivalents to 0.8 equivalents, relative to 1 mol of racemic (2RS,12Z)-2-hydroxy-12-heptadecene.

The reaction temperature of the benzoylation may be any temperature at which the enzyme catalyst activity and stability can be maintained. For example, the reaction temperature of the benzoylation is preferably from 20° C. to 80° C., and from the standpoint of enzyme catalyst activity and stability, particularly preferably from 40° C. to 60° C.

The reaction solution of the benzoylation may have any pH value at which the enzyme catalyst activity and stability can be maintained. For example, the reaction solution of the benzoylation has a pH value of preferably from 5 to 9, and from the standpoint of enzyme catalyst activity and stability, particularly preferably from 6 to 8. To adjust the pH value of the reaction solution, the reaction system may contain a phosphate buffer, an acetate buffer, a borate buffer, an ammonium chloride buffer or the like.

The solution produced by the benzoylation may be subjected to filteration, centrifugation or the other separation technique to remove the enzyme catalyst. The solvent may be then removed under reduced pressure or under normal pressure to produce a mixture of optically active (2R,12Z)-2-benzoyloxy-12-heptadecene (R,Z-2) and optically active (2S,12Z)-2-hydroxy-12-heptadecene (S,Z-1).

The mixture of optically active (2R,12Z)-2-benzoyloxy-12-heptadecene (R,Z-2) and optically active (2S,12Z)-2-hydroxy-12-heptadecene (S,Z-1) is heated to distill only the optically active (2S,12Z)-2-hydroxy-12-heptadecene (S,Z-1), leaving the optically active (2R,12Z)-2-benzoyloxy-12-heptadecene (R,Z-2) behind for separation.

Examples of the distillation apparatus include batch system distillation apparatuses and continuous distillation apparatuses. A simple distillation apparatus without a packing can be used for separation, but a rectification apparatus filled with a packing such as Raschig rings, Lessing rings, Pall rings, McMahon packing and Sulzer packing can also be used.

The distillation is preferably carried out under reduced pressure with heating. The pressure is preferably 0.013 to 1.333 KPa. The pressure is such a pressure as to allow the optically active (2S,12Z)-2-hydroxy-12-heptadecene (S,Z-1) to be distilled preferably at 69 to 190° C.

(Z)-2-Benzoyloxy-12-heptadecene represented by Formula (RS,Z-2) below is an equimolar mixture of optically active (2R,12Z)-2-benzoyloxy-12-heptadecene (R,Z-2) and optically active (2S,12Z)-2-benzoyloxy-12-heptadecene represented by Formula (S,Z-2) below. The optically active (2R,12Z)-2-benzoyloxy-12-heptadecene (R,Z-2) can be produced by the above production method, while the optically active (2S,12Z)-2-benzoyloxy-12-heptadecene (S,Z-2) can be similarly produced by using a lipase which specifically catalyzes the benzoylation of (2S,12Z)-2-hydroxy-12-heptadecene.

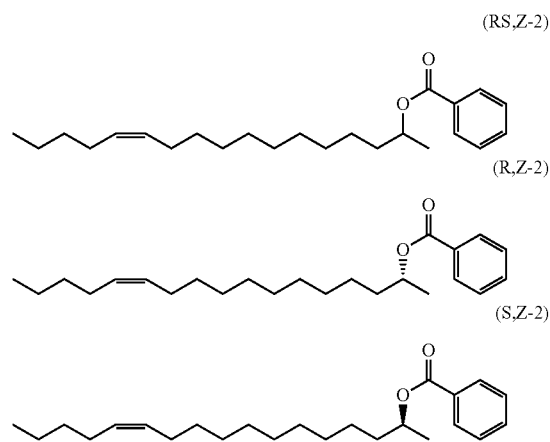

The optically active (2S,12Z)-2-hydroxy-12-heptadecene (S,Z-1) obtained by the distillation can be acetylated by a known method to produce (2S,12Z)-2-acetoxy-12-heptadecene, which is the sex pheromone of the pistachio twig borer and is represented by Formula (S,Z-3):

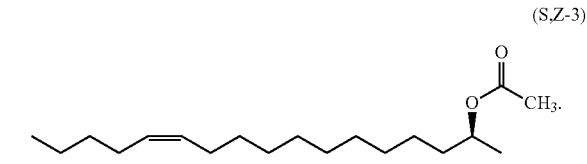 [SMILES: CCCC/C=C\CCCCCCCCC[C@H](C)OC(C)=O]

The method of acetylating the optically active (2S,12Z)-2-hydroxy-12-heptadecene (S,Z-1) to produce the (2S,12Z)-2-acetoxy-12-heptadecene (S,Z-3) is not particularly limited, and may include a method of reacting an alcohol compound with an acetylating agent in the presence of a base or an acid.

Examples of the acetylating agent include acetic halides represented by CH₃COX wherein X represents a halogen atom, which is preferably Cl, Br or I; acetic anhydride; acetic acid; and acetate esters.

Examples of the base include amine compounds such as trimethylamine, triethylamine, pyridine, dimethylaniline, N,N-diisopropylethylamine and 4-dimethylaminopyridine; and metal alkoxides such as potassium t-butoxide and sodium methoxide. The base may be used singly or in combination of two or more bases.

Examples of the acid include mineral acids such as hydrochloric acid and sulfuric acid; aromatic sulfonic acids such as benzenesulfonic acid and p-toluenesulfonic acid; Lewis acids such as boron trifluoride etherate and tetraisopropyl orthotitanate; and cation exchange resins such as Dowex 50 and Amberlyst-15. The acid may be used singly or in combination of two or more acids.

Preferred examples of the acetylation of optically active (2S,12Z)-2-hydroxy-12-heptadecene (S,Z-1) include reaction with acetyl chloride in the presence of a base such as pyridine or triethylamine; reaction with acetic anhydride in the presence of a base such as pyridine or trimethylamine; dehydration reaction with acetic acid in the presence of an acid catalyst such as sulfuric acid or p-toluenesulfonic acid; and transesterification reaction with an acetate ester such as methyl acetate or ethyl acetate in the presence of an acid catalyst such as sulfuric acid or p-toluenesulfonic acid or in the presence of a base catalyst such as potassium t-butoxide or sodium methoxide. From the standpoint of reactivity and the suppression of isomerization, preferred acetylation is the reaction with acetic anhydride in the presence of a base such as pyridine or triethylamine.

In the acetylation through reaction with acetyl chloride or acetic anhydride in the presence of a base, the amount of acetyl chloride or acetic anhydride to be used is preferably from 1.0 equivalent to 3.0 equivalents, and from the standpoint of reactivity and cost efficiency, particularly preferably from 1.5 equivalents to 2.0 equivalents, relative to 1 mol of optically active (2S,12Z)-2-hydroxy-12-heptadecene. The amount of the base to be used is preferably from 1.0 equivalent to 5.0 equivalents, and from the standpoint of reactivity and cost efficiency, particularly preferably from 1.5 equivalents to 2.0 equivalents, relative to 1 mol of optically active (2S,12Z)-2-hydroxy-12-heptadecene.

In the acetylation through dehydration reaction with acetic acid in the presence of an acid catalyst, the amount of acetic acid to be used is preferably from 1.0 equivalent to 10.0 equivalents, and from the standpoint of reactivity and cost efficiency, particularly preferably from 2.0 equivalents to 5.0 equivalents, relative to 1 mol of optically active (2S,12Z)-2-hydroxy-12-heptadecene. The amount of the acid catalyst to be used is preferably from 0.01 equivalents to 1.0 equivalent, and from the standpoint of reactivity and cost efficiency, particularly preferably from 0.01 equivalents to 0.5 equivalents, relative to 1 mol of optically active (2S,12Z)-2-hydroxy-12-heptadecene.

In the acetylation through transesterification reaction with an acetate ester in the presence of an acid catalyst or a base catalyst, the amount of the acetate ester to be used is preferably from 1.0 equivalent to 10.0 equivalents, and from the standpoint of reactivity and cost efficiency, particularly preferably from 2.0 equivalents to 5.0 equivalents, relative to 1 mol of optically active (2S,12Z)-2-hydroxy-12-heptadecene. The amount of the acid or base catalyst to be used is preferably from 0.01 equivalents to 1.0 equivalent, and from the standpoint of reactivity and cost efficiency, particularly preferably from 0.01 equivalents to 0.5 equivalents, relative to 1 mol of optically active (2S,12Z)-2-hydroxy-12-heptadecene.

Examples of the solvent used for the acetylation include halogenated solvents such as dichloromethane and chloroform; ethers such as tetrahydrofuran and diethyl ether; nitriles such as acetonitrile and benzonitrile; ketones such as acetone and methyl ethyl ketone; esters such as methyl acetate and ethyl acetate; and hydrocarbons such as hexane and toluene. From the standpoint of reactivity, particularly preferred are halogenated solvents, ethers and nitriles.

The amount of the solvent used for the acetylation is preferably from 0 g to 3,000 g, and from the standpoint of reactivity and cost efficiency, particularly preferably from 500 g to 1,500 g, relative to 1 mol of optically active (2S,12Z)-2-hydroxy-12-heptadecene.

The reaction temperature of the acetylation is preferably from 0° C. to 100° C., and from the standpoint of reactivity and yield, particularly preferably from 25° C. to 80° C.

The optical purity of the obtained optically active (2S,12Z)-2-hydroxy-12-heptadecene (S,Z-1) can be determined by gas chromatographic analysis by using a chiral column such as Cyclosil-β (Agilent Technologies).

The optical purity of the optically active (2R,12Z)-2-benzoyloxy-12-heptadecene (R,Z-2) obtained by the distillation can be determined in the method comprising the steps of hydrolyzing (2R,12Z)-2-Benzoyloxy-12-heptadecene (R,Z-2) in the presence of a base such as sodium hydroxide, potassium hydroxide or potassium carbonate and an alcohol such as methanol or ethanol to produce (2R,12Z)-2-hydroxy-12-heptadecene (S,Z-1); acetylating the (2R,12Z)-2-hydroxy-12-heptadecene (S,Z-1) by the above known method to obtain optically active (2R,12Z)-2-acetoxy-12-heptadecene; and analyzing the optically active (2R,12Z)-2-acetoxy-12-heptadecene by gas chromatography with a chiral column such as Cyclosil-β (Agilent Technologies).

As described above, the optically active (2S,12Z)-2-hydroxy-12-heptadecene (S,Z-1) in the mixture of optically active (2R,12Z)-2-benzoyloxy-12-heptadecene (R,Z-2) and optically active (2S,12Z)-2-hydroxy-12-heptadecene (S,Z-1) can be acetylated to produce optically active (2S,12Z)-2-acetoxy-12-heptadecene (S,Z-3). Separately, the configuration of optically active (2R,12Z)-2-benzoyloxy-12-heptadecene (R,Z-2) can be inverted by a known method to produce optically active (2S,12Z)-2-acetoxy-12-heptadecene (S,Z-3).

For example, (2R,12Z)-2-benzoyloxy-12-heptadecene (R,Z-2) is hydrolyzed preferably in the presence of an acid such as hydrochloric acid, sulfuric acid, trifluoroacetic acid or p-toluenesulfonic acid, or a base such as potassium hydroxide, sodium hydroxide or potassium carbonate to produce (2R,12Z)-2-hydroxy-12-heptadecene; and the hydroxy group of the obtained (2R,12Z)-2-hydroxy-12-heptadecene is mesylated (methanesulfonylated) or tosylated (p-toluenesulfonylated) and then is acetoxylated by reaction with an acetoxylating agent. Examples of the acetoxylating agent include metal acetates represented by $CH_3CO_2Y$ wherein Y represents a metal atom, which is preferably Na, K or Li.

In a specific example, (2R,12Z)-2-benzoyloxy-12-heptadecene (R,Z-2) may be reacted in the presence of a base such as sodium hydroxide or potassium carbonate and an alcohol such as methanol and ethanol to produce (2R,12Z)-2-hydroxy-12-heptadecene; and the (2R,12Z)-2-hydroxy-12-heptadecene may be reacted with methanesulfonyl chloride or p-toluenesulfonyl chloride in the presence of a base such as pyridine or triethylamine, and then may be reacted with an acetoxylating agent (preferably a metal acetate such as sodium acetate and potassium acetate) to produce (2S,12Z)-2-acetoxy-12-heptadecene (S,Z-3), which is the sex pheromone of pistachio twig borer.

When the (2S,12Z)-2-acetoxy-12-heptadecene (S,Z-3) obtained by the configuration inversion has a lower optical purity than an intended optical purity, the optical purity can be enhanced by the method comprising the steps of: hydrolyzing the (2S,12Z)-2-acetoxy-12-heptadecene in the presence of alkali to obtain (2S,12Z)-2-hydroxy-12-heptadecene (S,Z-1); and subjecting the obtained (2S,12Z)-2-hydroxy- 12-heptadecene (S,Z-1) to another optical resolution after reaction with vinyl benzoate in the presence of a lipase that is an esterase produced by microorganisms.

The present invention will hereinafter be described on basis of Examples and Comparative Examples. However, it should not be construed that the present invention is limited to or by Examples.

EXAMPLES

Example 1

Production of Optically Active (2R,12Z)-2-benzoyloxy-12-heptadecene (R,Z-2) and Optically Active (2S,12Z)-2-hydroxy-12-heptadecene (S,Z-1)

Racemic (2RS,12Z)-2-hydroxy-12-heptadecene (254.5 g: 1.0 mol), vinyl benzoate (148.2 g: 1.0 mol: 1.0 equivalent), n-hexane (850.0 ml, 561.0 g) and Novozym435 (30.0 g: 30000 units, manufactured by Novozymes) were placed in a reaction vessel with a stirrer, a cooling condenser and a thermometer, and stirred at 50° C. Monitoring the reaction by gas chromatography with a column of DB-5 (product by Agilent Technologies, length: 30 m, inner diameter: 0.25 mm, film thickness: 0.25 μm) in which the column temperature was increased from 150° C. to 300° C. at a rate of 10° C./min, the completion of the reaction was confirmed. After the completion of the reaction, the reaction solution was filtrated to remove the enzyme catalyst, washed with 3% by weight aqueous sodium hydrogen carbonate solution (250.0 g), and subjected to removal of the solvent under reduced pressure. As a result, a concentrated reaction mixture (357.5 g), which was a mixture of (2R,12Z)-2-benzoyloxy-12-heptadecene and (2S,12Z)-2-hydroxy-12-heptadecene, was obtained.

The ratio of the (2R,12Z)-2-benzoyloxy-12-heptadecene to the (2S,12Z)-2-hydroxy-12-heptadecene in the concentrated reaction mixture was determined by $^1$H-NMR, and found to be 50.1:49.9.

The (2S,12Z)-2-hydroxy-12-heptadecene alone was distilled from the concentrated reaction mixture for isolation by using a simple distillation apparatus without a packing. As a result, (2S,12Z)-2-hydroxy-12-heptadecene (b.p.: 117-119° C./0.13 KPa, 117.8 g, 0.46 mol, yield: 46.3%) was obtained. In addition, (2R,12Z)-2-benzoyloxy-12-heptadecene (174.6 g, 0.49 mol, yield: 48.7%) was obtained as the distillation residue.

The structures of the obtained (2S,12Z)-2-hydroxy-12-heptadecene and (2R,12Z)-2-benzoyloxy-12-heptadecene were identified by $^1$H nuclear magnetic resonance spectra, $^{13}$C nuclear magnetic resonance spectra, mass spectra and IR spectra.

The compositions of the obtained distillate fraction and residue analyzed by gas chromatography are shown in Table 1.

<Spectral Data of (2S,12Z)-2-hydroxy-12-heptadecene (S,Z-1)>

(Nuclear magnetic resonance spectrum) $^1$H NMR (500 MHz, CDCl$_3$): δ 0.89 (3H, t), 1.18 (3H, d), 1.22-1.50 (20H, m), 1.53 (1H, d), 1.98-2.06 (4H, m), 3.78 (1H, tq), 5.34 (2H, dt), $^{13}$C NMR (126 MHz, CDCl$_3$): δ 13.97, 22.32, 23.44, 25.75, 26.89, 27.17, 29.27, 29.51, 29.55, 29.59, 29.63, 29.74

(Mass spectrum) EI (70 eV): m/z 254 (M$^+$), 236 (M$^+$-H$_2$O), 194, 180, 166, 152, 138, 124, 110, 96, 82, 64, 55, 41

(Infrared absorption spectrum) (liquid film): ν (cm$^{-1}$) 722, 933, 1067, 1115, 1375, 1465, 2853, 2925, 2958, 3005, 3328

<Spectral Data of (2R,12Z)-2-benzoyloxy-12-heptadecene (R,Z-2)>

(Nuclear magnetic resonance spectrum) $^1$H NMR (500 MHz, CDCl$_3$): δ 0.90 (3H, t), 1.24-1.36 (21H, m), 1.56-1.65 (1H, m), 1.70-1.79 (1H, m), 1.99-2.05 (4H, m), 5.16 (1H, tq), 5.34 (2H, dt), 4.43 (2H, dd), 7.54 (1H, dd), 8.03 (2H, d), $^{13}$C NMR (126 MHz, CDCl$_3$): δ 13.99, 20.06, 22.32, 25.42, 26.90, 27.17, 29.26, 29.47, 29.50, 29.52, 29.74, 31.95, 36.04, 71.72, 128.24, 129.49, 129.82, 129.86, 130.93, 132.64, 166.19

(Mass spectrum) EI (70 eV): m/z 236 (M$^+$-PhCO$_2$H), 194, 173, 152, 123, 105, 82, 55

(Infrared absorption spectrum) (liquid film): ν (cm$^{-1}$) 711, 1026, 1070, 1110, 1314, 1355, 1378, 1451, 1585, 1603, 1717, 2854, 2926

TABLE 1

|  | (2S,12Z)-2-Hydroxy-12-heptadecene Formula (S,Z-1) (GC area %) | (2R,12Z)-2-Benzoyloxy-12-heptadecene Formula (R,Z-2) (GC area %) |
|---|---|---|
| Fraction 1 | 94.87 | 0.82 |
| Residue | 0.99 | 93.65 |

Example 2

Production of (2S,12Z)-2-acetoxy-12-heptadecene (S,Z-3)

The (2S,12Z)-2-hydroxy-12-heptadecene (117.8 g, 0.46 mol) obtained in Example 1, acetic anhydride (70.4 g, 0.69 mol, 1.5 equivalents), pyridine (72.8 g, 0.92 mol, 2.0 equivalents) and methylene chloride (500.0 g) were placed in a reaction vessel with a stirrer, a cooling condenser and a thermometer, and stirred at 35° C. The reaction was monitored by gas chromatography with a column of DB-5 (product of Agilent Technologies, length: 30 m, inner diameter: 0.25 mm, film thickness: 0.25 μm) in which the column temperature was increased from 150° C. to 300° C. at a rate of 10° C./min After the completion of the reaction, the reaction solution was subjected to addition of water (500.0 g) to stop the reaction, and extracted with diethyl ether (500.0 g). The obtained organic phase was washed with a 10% by weight aqueous hydrochloric acid solution (500.0 g) and a 3% by weight aqueous sodium hydrogen carbonate solution (500.0 g), and subjected to removal of the solvent under reduced pressure. The residue was distilled under reduced pressure to obtain (2S,12Z)-2-acetoxy-12-heptadecene (b.p.: 122-124° C./0.13 KPa, 132.8 g, 0.45 mol, yield: 97.4%).

The structure of the obtained (2S,12Z)-2-acetoxy-12-heptadecene was identified by a $^1$H nuclear magnetic resonance spectrum, a $^{13}$C nuclear magnetic resonance spectrum, a mass spectrum and an IR spectrum. The acetate was subjected to gas chromatography with a chiral column of Cyclosil-β (Agilent Technologies, length: 30 m, inner diameter: 0.25 mm, film thickness: 0.25 μm) in which the column temperature was maintained at 100° C. for 5 minutes and then raised to 200° C. at a rate of 5° C./min. As a result, an optical purity (enantiomeric excess: ee) was found to be 100.0%.

In order to determine the optical activity of the optically active (2R,12Z)-2-benzoyloxy-12-heptadecene obtained in Example 1, it was hydrolyzed and then acetylated to produce (2R,12Z)-2-acetoxy-12-heptadecene. The obtained acetate was subjected to gas chromatography with a chiral column of Cyclosil-β (product of Agilent Technologies, length: 30 m, inner diameter: 0.25 mm, film thickness: 0.25 μm) in which the column temperature was maintained at 100° C. for 5 minutes and then raised to 200° C. at a rate of 5° C./min. As a result, an optical purity (enantiomeric excess: ee) was found to be 88.6%.

<Spectral Data of (2S,12Z)-2-acetoxy-12-heptadecene (S,Z-3)>

(Nuclear magnetic resonance spectrum) $^1$H NMR (500 MHz, CDCl$_3$): δ 0.89 (3H, t), 1.19 (3H, d), 1.24-1.62 (20H, m), 1.99-2.04 (7H, m), 4.88 (1H, tq), 5.34 (2H, dt), $^{13}$C NMR (126 MHz, CDCl$_3$): δ 13.97, 19.29, 21.35, 22.32, 25.38, 26.89, 27.16, 29.25, 29.43, 29.48, 29.50, 29.62, 29.73, 31.94, 35.90, 71.04, 129.82, 129.84, 170.75 (Mass spectrum) EI (70 eV): m/z 281 (M$^+$-CH$_3$), 236 (M$^+$-CH$_3$CO$_2$H), 194, 180, 166, 152, 138, 124, 110, 96, 82, 67, 43

(Infrared absorption spectrum) (liquid film): ν (cm$^{-1}$) 722, 951, 1020, 1371, 1465, 1739, 2854, 2926, 3004

Example 3

Production of Optically Active (2R,12Z)-2-benzoyloxy-12-heptadecene (R,Z-2) and Optically Active (2S,12Z)-2-hydroxy-12-heptadecene (S,Z-1)

The reaction and work-up were carried out in the same manner as in Example 1 by using racemic (2RS,12Z)-2-hydroxy-12-heptadecene (254.5 g: 1.0 mol), vinyl benzoate (88.9 g: 0.6 mol: 0.6 equivalents), n-hexane (850.0 ml, 561.0 g) and Novozym435 (30.0 g: 30000 units, manufactured by Novozymes).

The ratio of the (2R,12Z)-2-benzoyloxy-12-heptadecene to the (2S,12Z)-2-hydroxy-12-heptadecene in the concentrated reaction mixture obtained (336.7 g) was determined by $^1$H-NMR, and found to be 50.0:50.0.

The (2S,12Z)-2-hydroxy-12-heptadecene alone was distilled from the concentrated reaction mixture for isolation by using a simple distillation apparatus without a packing. As a result, (2S,12Z)-2-hydroxy-12-heptadecene (122.1 g, 0.48 mol, yield: 48.0%) was obtained. In addition, (2R,12Z)-2-benzoyloxy-12-heptadecene (169.2 g, 0.47 mol, yield: 47.2%) was obtained as the distillation residue.

The structures of the obtained (2S,12Z)-2-hydroxy-12-heptadecene and (2R,12Z)-2-benzoyloxy-12-heptadecene were identified by $^1$H nuclear magnetic resonance spectra, $^{13}$C nuclear magnetic resonance spectra, mass spectra and IR spectra.

The compositions of the obtained distillate fraction and residue analyzed by gas chromatography are shown in Table 2.

TABLE 2

|  | (2S,12Z)-2-Hydroxy-12-heptadecene Formula (S,Z-1) (GC area %) | (2R,12Z)-2-Benzoyloxy-12-heptadecene Formula (R,Z-2) (GC area %) |
| --- | --- | --- |
| Fraction 1 | 93.33 | 0.96 |
| Residue | 0.70 | 95.59 |

Example 4

Production of (2S,12Z)-2-acetoxy-12-heptadecene (S,Z-3)

(2S,12Z)-2-Acetoxy-12-heptadecene was produced in the same manner as in Example 2 by using the (2S,12Z)-2-hydroxy-12-heptadecene (122.1 g, 0.48 mol) obtained in Example 3. As a result, (2S,12Z)-2-acetoxy-12-heptadecene (136.6 g, 0.46 mol, yield: 96.0%) was obtained.

The structure of the obtained (2S,12Z)-2-acetoxy-12-heptadecene was identified by a $^1$H nuclear magnetic resonance spectrum, a $^{13}$C nuclear magnetic resonance spectrum, a mass spectrum and an IR spectrum. The acetate was subjected to gas chromatography with a chiral column of Cyclosil-β (product of Agilent Technologies, length: 30 m, inner diameter: 0.25 mm, film thickness: 0.25 μm) in which the temperature was maintained at 100° C. for 5 minutes and then raised to 200° C. at a rate of 5° C./min. As a result, an optical purity (enantiomeric excess: ee) was found to be 100.0%.

In order to determine the optical activity of the optically active (2R,12Z)-2-benzoyloxy-12-heptadecen obtained in Example 3, it was hydrolyzed and then acetylated to produce (2R,12Z)-2-acetoxy-12-heptadecene. The obtained acetate was subjected to gas chromatography with a chiral column of Cyclosil-β (product of Agilent Technologies, length: 30 m, inner diameter: 0.25 mm, film thickness: 0.25 μm) in which the column temperature was maintained at 100° C. for 5 minutes and then raised to 200° C. at a rate of 5° C./min. As a result, an optical purity (enantiomeric excess: ee) was found to be 90.8%.

Example 5

Production of Optically Active (2R,12Z)-2-benzoyloxy-12-heptadecene (R,Z-2) and Optically Active (2S,12Z)-2-hydroxy-12-heptadecene (S,Z-1)

The reaction and work-up were carried out in the same manner as in Example 1 by using racemic (2RS,12Z)-2-hydroxy-12-heptadecene (254.5 g: 1.0 mol), vinyl benzoate (88.9 g: 0.6 mol: 0.6 equivalents), n-hexane (850.0 ml, 561.0 g) and Novozym435 (10.0 g: 10000 units, manufactured by Novozymes) to obtain a concentrated reaction mixture (325.8 The ratio of the (2R,12Z)-2-benzoyloxy-12-heptadecene to the (2S,12Z)-2-hydroxy-12-heptadecene in the concentrated reaction mixture was determined by $^1$H NMR and found to be 50.0:50.0.

The (2S,12Z)-2-hydroxy-12-heptadecene alone was distilled from the concentrated reaction mixture by using a simple distillation apparatus without a packing. As a result, (2S,12Z)-2-hydroxy-12-heptadecene (120.4 g, 0.47 mol, yield: 47.3%) was obtained. In addition, (2R,12Z)-2-benzoyloxy-12-heptadecene (171.8 g, 0.48 mol, yield: 47.9%) was obtained as the distillation residue.

The structures of the obtained (2S,12Z)-2-hydroxy-12-heptadecene and (2R,12Z)-2-benzoyloxy-12-heptadecene were identified by $^1$H nuclear magnetic resonance spectra, $^{13}$C nuclear magnetic resonance spectra, mass spectra and IR spectra.

The compositions of the obtained distillate fraction and residue analyzed by gas chromatography are shown in Table 3.

TABLE 3

|  | (2S,12Z)-2-Hydroxy-12-heptadecene Formula (S,Z-1) (GC area %) | (2R,12Z)-2-Benzoyloxy-12-heptadecene Formula (R,Z-2) (GC area %) |
| --- | --- | --- |
| Fraction 1 | 95.05 | 0.56 |
| Residue | 0.58 | 96.84 |

Example 6

Production of (2S,12Z)-2-acetoxy-12-heptadecene (S,Z-3)

(2S,12Z)-2-Acetoxy-12-heptadecene was produced in the same manner as in Example 2 by using the (2S,12Z)-2-hydroxy-12-heptadecene (120.4 g, 0.47 mol) obtained in Example 5. As a result, (2S,12Z)-2-acetoxy-12-heptadecene (132.3 g, 0.46 mol, yield: 95.0%) was obtained.

The structure of the obtained (2S,12Z)-2-acetoxy-12-heptadecene was identified by a $^1$H nuclear magnetic resonance spectrum, a $^{13}$C nuclear magnetic resonance spectrum, a mass spectrum and an IR spectrum. The acetate was analyzed by gas chromatography with a chiral column of Cyclosil-β (length: 30 m, inner diameter: 0.25 mm, film thickness: 0.25 μm) in which the column temperature was maintained at 100° C. for 5 minutes and then raised to 200° C. at a rate of 5° C./min, and found to be an optical purity (enantiomeric excess: ee) of 100.0%.

In order to determine the optical activity of the optically active (2R,12Z)-2-benzoyloxy-12-heptadecene obtained in Example 5, it was hydrolyzed and then acetylated to produce (2R,12Z)-2-acetoxy-12-heptadecene. The obtained acetate was analyzed by gas chromatography with a chiral column of Cyclosil-β (product of Agilent Technologies, length: 30 m, inner diameter: 0.25 mm, film thickness: 0.25 μm) in which the column temperature was maintained at 100° C. for 5 minutes and then raised to 200° C. at a rate of 5° C./min, and found to be optical purity (enantiomeric excess: ee) of 90.0%.

Example 7

Production of (2S,12Z)-2-acetoxy-12-heptadecene (S,Z-3) from (2R,12Z)-2-benzoyloxy-12-heptadecene (R,Z-2)

(2R,12Z)-2-Benzoyloxy-12-heptadecene (148.25 g: 0.5 mol) and methanol (300.0 g) were placed in a reaction vessel with a stirrer, a cooling condenser and a thermometer, and stirred at 35° C. The mixture was subjected to dropwise addition of 10% by weight aqueous sodium hydroxide solution (500.0 g) at 35 to 45° C., and then stirred at 40 to 45° C. for 3 hours. The reaction solution was cooled to room temperature and extracted with diethyl ether (300.0 g). The organic phase was washed with 5% by weight aqueous sodium chloride solution, and then subjected to removal of the solvent under reduced pressure. The residue was distilled under reduced pressure to obtain (2R,12Z)-2-hydroxy-12-heptadecene (b.p.: 115-118° C. (0.13 KPa), 124.9 g, 0.49 mol, yield: 98.0%).

<Spectral Data of (2R,12Z)-2-hydroxy-12-heptadecene>

(Nuclear magnetic resonance spectrum) $^1$H NMR (500 MHz, CDCl$_3$): δ 0.88 (3H, t), 1.18 (3H, d), 1.20-1.49 (20H, m), 1.50 (1H, d), 1.98-2.09 (4H, m), 3.72 (1H, tq), 5.34 (2H, dt), $^{13}$C NMR (126 MHz, CDCl$_3$): δ 13.98, 22.34, 23.46, 25.73, 26.89, 27.17, 29.29, 29.51, 29.54, 29.59, 29.64, 29.74

(Mass spectrum) EI (70 eV): m/z 254 (M$^+$), 236 (M$^+$-H$_2$O), 194, 180, 166, 152, 138, 124, 110, 96, 82, 64, 55, 41

(Infrared absorption spectrum) (liquid film): ν (cm$^{-1}$) 725, 935, 1064, 1118, 1374, 1466, 2852, 2925, 2958, 3007, 3328

Subsequently, (2R,12Z)-2-hydroxy-12-heptadecene (124.9 g, 0.49 mol), triethylamine (60.7 g, 0.60 mol) and dichloromethane (600.0 g) were placed in a reaction vessel with a stirrer, a cooling condenser and a thermometer, and subjected to dropwise addition of methanesulfonyl chloride (63.0 g, 0.55 mol) at 0 to 5° C. After the dropwise addition, the mixture was stirred at 0 to 5° C. for 2 hours, and subjected to addition of 5% by weight aqueous sodium hydrogen carbonate solution (250.0 g) to stop the reaction. The reaction solution was extracted with diethyl ether (500.0 g). The obtained organic phase was washed with 0.5% by weight aqueous hydrochloric acid solution (300.0 g), 5% by weight aqueous sodium hydrogen carbonate solution (250.0 g), and 5% by weight aqueous sodium chloride solution (250.0 g), and then subjected to removal of the solvent under reduced pressure to obtain a concentrated reaction mixture (163.5 g). The formation of (2R,12Z)-2-methanesulfonyloxy-12-heptadecene was identified by $^1$H NMR. The concentrated reaction mixture was used for the subsequent reaction without purification.

<Spectral Data of (2R,12Z)-2-methanesulfonyloxy-12-heptadecene>

(Nuclear magnetic resonance spectrum) $^1$H NMR (500 MHz, CDCl$_3$): δ 0.90 (3H, t), 1.22-1.30 (18H, m), 1.40 (3H, d), 1.59 (1H, dt), 1.70 (1H, dt) 1.99-2.03 (4H, m), 2.99 (3H, s), 4.79 (1H, tq), 5.32 (2H, dt)

Next, (2R,12Z)-2-methanesulfonyloxy-12-heptadecene (163.5 g), potassium acetate (78.5 g, 0.8 mol) and dimethylacetamide (500.0 g) were placed in a reaction vessel with a stirrer, a cooling condenser and a thermometer, and stirred at 60° C. for 20 hours. The reaction solution was cooled, and then subjected to addition of water (300.0 g) to stop the reaction. The reaction solution was extracted with diethyl ether (350.0 g). The organic phase was washed with 5% by weight aqueous sodium chloride solution (250.0 g), and then subjected to solvent removal under reduced pressure. The residue was distilled under reduced pressure to obtain (2S,12Z)-2-acetoxy-12-heptadecene (b.p.: 119-122° C./0.13 KPa, 135.8 g, 0.46 mol, yield: 93.5%).

The obtained (2S,12Z)-2-acetoxy-12-heptadecene was analyzed by gas chromatography with a chiral column of Cyclosil-β (product of Agilent Technologies, length: 30 m, inner diameter: 0.25 mm, film thickness: 0.25 μm) in which the temperature was maintained at 100° C. for 5 minutes and then raised to 200° C. at a rate of 5° C./min, and found to be an optical purity (enantiomeric excess: ee) of 91.3%.

Comparative Example 1

Production of Optically Active (2R,12Z)-2-acetoxy-12-heptadecene and Optically Active (2S,12Z)-2-hydroxy-12-heptadecene (S,Z-1)

Racemic (2RS,12Z)-2-hydroxy-12-heptadecene (25.4 g: 0.1 mol), vinyl acetate (8.6 g: 0.1 mol: 1.0 equivalent), n-hexane (85.0 g) and Novozym435 (3.0 g: 3,000 unit, manufactured by Novozymes) were placed in a reaction vessel with a stirrer, a cooling condenser and a thermometer, and stirred at 50° C. Monitoring the reaction by gas chromatography with a column of DB-5 (length: 30 m, inner diameter: 0.25 mm, film thickness: 0.25 μm) in which the temperature was increased from 150° C. to 300° C. at a rate of 10° C./min, the completion of the reaction was confirmed. After the completion of the reaction, the reaction solution was filtrated to remove the enzyme catalyst and washed with 3% by weight aqueous sodium hydrogen carbonate solution (25.0 g), and subjected to solvent removal under reduced pressure to obtain a concentrated reaction mixture (32.4 g).

The ratio of the (2R,12Z)-2-acetoxy-12-heptadecene to the (2S,12Z)-2-hydroxy-12-heptadecene in the concentrated reaction mixture was determined by $^1$H-NMR, and found to be 56.3:43.7.

The concentrated reaction mixture was distilled by using a simple distillation apparatus without a packing to separate the (2S,12Z)-2-hydroxy-12-heptadecene from the (2R,12Z)-2-acetoxy-12-heptadecene. The compositions of the obtained distillate fractions analyzed by gas chromatography are shown in Table 4.

TABLE 4

| Fraction | (2R,12Z)-2-Acetoxy-12-heptadecene (GC area %) | (2S,12Z)-2-Hydroxy-12-heptadecene Formula (S,Z-1) (GC area %) |
|---|---|---|
| 1 | 55.21 | 36.22 |
| 2 | 49.77 | 45.44 |
| 3 | 35.88 | 60.40 |
| 4 | 12.34 | 82.21 |
| 5 | 4.39 | 90.03 |

<Spectral Data of (2R,12Z)-2-acetoxy-12-heptadecene>

(Nuclear magnetic resonance spectrum) $^1$H NMR (500 MHz, CDCl$_3$): δ 0.89 (3H, t), 1.19 (3H, d), 1.24-1.62 (20H, m), 19.9-2.04 (7H, m), 4.88 (1H, tq), 5.34 (2H, dt), $^{13}$C-NMR (126 MHz, CDCl$_3$): δ 13.97, 19.29, 21.35, 22.32, 25.38, 26.89, 27.16, 29.25, 29.43, 29.48, 29.50, 29.62, 29.73, 31.94, 35.90, 71.04, 129.82, 129.84, 170.75

(Mass spectrum) EI (70 eV): m/z 281 (M$^+$-CH$_3$), 236 (M$^+$-CH$_3$CO$_2$H), 194, 180, 166, 152, 138, 124, 110, 96, 82, 67, 43 (Infrared absorption spectrum) (liquid film): ν (cm$^{-1}$) 722, 951, 1020, 1371, 1465, 1739, 2854, 2926, 3004

Comparative Example 2

Production of Optically Active (2R,12Z)-2-acetoxy-12-heptadecene and Optically Active (2S,12Z)-2-hydroxy-12-heptadecene (S,Z-1)

The reaction and work-up were carried out in the same manner as in Comparative Example 1 by using racemic (2RS,12Z)-2-hydroxy-12-heptadecene (25.4 g: 0.1 mol), vinyl acetate (5.2 g: 0.06 mol: 0.6 equivalents), n-hexane (85.0 g) and Novozym435 (3.0 g: 3,000 units, manufactured by Novozymes) in a reaction vessel with a stirrer, a cooling condenser and a thermometer to obtain a concentrated reaction mixture (28.7 g).

The ratio of the (2R,12Z)-2-acetoxy-12-heptadecene to the (2S,12Z)-2-hydroxy-12-heptadecene in the concentrated reaction mixture was determined by $^1$H NMR, and found to be 47.2:52.8.

The concentrated reaction mixture obtained was distilled by using a simple distillation apparatus without a packing to separate the (2S,12Z)-2-hydroxy-12-heptadecene from the (2R,12Z)-2-acetoxy-12-heptadecene. The compositions of the obtained fractions analyzed by gas chromatography are shown in Table 5.

TABLE 5

| Fraction | (2R,12Z)-2-Acetoxy-12-heptadecene (GC area %) | (2S,12Z)-2-Hydroxy-12-heptadecene Formula (S,Z-1) (GC area %) |
|---|---|---|
| 1 | 62.65 | 28.38 |
| 2 | 56.81 | 38.76 |
| 3 | 33.79 | 65.38 |
| 4 | 10.34 | 85.11 |
| 5 | 2.39 | 93.48 |

Comparative Example 3

Production of Optically Active (2R,12Z)-2-butanoyloxy-12-heptadecene and Optically Active (2S,12Z)-2-hydroxy-12-heptadecene (S,Z-1)

The reaction and work-up were carried out in the same manner as in Comparative Example 1 by using racemic (2RS,12Z)-2-hydroxy-12-heptadecene (25.4 g: 0.1 mol), vinyl butyrate (6.8 g: 0.06 mol: 0.6 equivalents), n-hexane (85.0 g) and Novozym435 (3.0 g: 3,000 units, manufactured by Novozymes) in a reaction vessel with a stirrer, a cooling condenser and a thermometer to obtain a concentrated reaction mixture (29.8 g).

The ratio of the (2R,12Z)-2-butanoyloxy-12-heptadecene to the (2S,12Z)-2-hydroxy-12-heptadecene in the concentrated reaction mixture was determined by $^1$H-NMR, and found to be 45.3:54.7.

The structures of the obtained (2R,12Z)-2-butanoyloxy-12-heptadecene and (2S,12Z)-2-hydroxy-12-heptadecene were identified by a $^1$H nuclear magnetic resonance spectrum, a $^{13}$C nuclear magnetic resonance spectrum, a mass spectrum and an IR spectrum.

The concentrated reaction mixture was distilled by using a simple distillation apparatus without a packing to separate the (2S,12Z)-2-hydroxy-12-heptadecene from the (2R,12Z)-2-butanoyloxy-12-heptadecene. The compositions of the obtained distillate fractions analyzed by gas chromatography are shown in Table 6.

<Spectral Data of (2R,12Z)-2-butanoyloxy-12-heptadecene>

(Nuclear magnetic resonance spectrum) $^1$H NMR (500 MHz, CDCl$_3$): δ 0.89 (3H, t), 0.94 (3H, t), 1.19 (3H, d), 1.24-1.59 (20H, m), 1.64 (2H, tq), 1.98-2.05 (4H, m), 2.25 (2H, t), 4.89 (1H, tq), 5.34 (2H, dt), $^{13}$C NMR (126 MHz, CDCl$_3$): δ 13.62, 13.97, 18.55, 19.99, 22.31, 25.39, 26.89, 27.16, 29.26, 29.42, 29.51, 29.55, 29.74, 31.94, 35.94, 36.61, 70.69, 129.82, 129.84, 173.35

(Mass spectrum) EI (70 eV): m/z 309 (M$^+$-CH$_3$), 236 (M$^+$-C$_3$H$_7$CO$_2$H), 194, 179, 152, 124, 96, 71, 55

(Infrared absorption spectrum) (liquid film): ν (cm$^{-1}$) 721, 949, 1043, 1090, 1127, 1185, 1256, 1378, 1464, 1733, 2855, 2926, 3003

TABLE 6

| Fraction | (2S,12Z)-2-Hydroxy-12-heptadecene Formula (S,Z-1) (GC area %) | (2R,12Z)-2-Butanoyloxy-12-heptadecene (GC area %) |
|---|---|---|
| 1 | 61.08 | 28.21 |
| 2 | 41.20 | 53.58 |
| 3 | 12.37 | 73.31 |
| 4 | 6.74 | 90.82 |
| 5 | 3.04 | 96.58 |

Comparative Example 4

Production of Optically Active (2R,12Z)-2-hexanoyloxy-12-heptadecene and Optically Active (2S,12Z)-2-hydroxy-12-heptadecene (S,Z-1)

The reaction and work-up were carried out in the same manner as in Comparative Example 1 by using racemic (2RS,12Z)-2-hydroxy-12-heptadecene (25.4 g: 0.1 mol), vinyl hexanate (8.5 g: 0.06 mol: 0.6 equivalents), n-hexane (85.0 g) and Novozym435 (3.0 g: 3,000 units, manufactured by Novozymes) in a reaction vessel with a stirrer, a cooling condenser and a thermometer to obtain a concentrated reaction mixture obtained (32.5 g).

The ratio of the (2R,12Z)-2-hexanoyloxy-12-heptadecene to the (2S,12Z)-2-hydroxy-12-heptadecene in the concentrated reaction mixture was determined by ¹H NMR, and found to be 47.1:52.9.

The structures of the obtained (2R,12Z)-2-hexanoyloxy-12-heptadecene and (2S,12Z)-2-hydroxy-12-heptadecene were identified by a ¹H nuclear magnetic resonance spectrum, a ¹³C nuclear magnetic resonance spectrum, a mass spectrum, and an IR spectrum.

The concentrated reaction mixture was distilled by using a simple distillation apparatus without a packing to separate the (2S,12Z)-2-hydroxy-12-heptadecene from the (2R,12Z)-2-hexanoyloxy-12-heptadecene. The compositions of the obtained distillate fractions analyzed by gas chromatography are shown in Table 7.

<Spectral Data of (2R,12Z)-2-hexanoyloxy-12-heptadecene>

(Nuclear magnetic resonance spectrum)¹H NMR (500 MHz, CDCl₃): δ 0.89 (6H, t), 1.19 (3H, d), 1.22-1.49 (23H, m), 1.52-1.65 (3H, m), 1.98-2.05 (4H, m), 2.25 (2H, t), 4.89 (1H, tq), 5.34 (2H, dt), ¹³C-NMR (126 MHz, CDCl₃): δ 13.89, 13.97, 19.99, 22.32, 24.77, 26.89, 27.16, 29.26, 29.43, 29.49, 29.51, 29.74, 31.29, 31.94, 34.70, 35.94, 70.69, 129.82, 129.84, 173.53

(Mass spectrum) EI (70 eV): m/z 337 (M⁺-CH₃), 236 (M⁺-C₅H₁₁CO₂H), 194, 180, 166, 138, 117, 99, 81, 55

(Infrared absorption spectrum) (liquid film): ν (cm⁻¹) 723, 1098, 1127, 1177, 1246, 1377, 1465, 1733, 2855, 2926, 2956

TABLE 7

| Fraction | (2S,12Z)-2-Hydroxy-12-heptadecene Formula (S,Z-1) (GC area %) | (2R,12Z)-2-Hexanoyloxy-12-heptadecene (GC area %) |
| --- | --- | --- |
| 1 | 75.20 | 17.95 |
| 2 | 48.88 | 45.97 |
| 3 | 4.05 | 90.57 |
| 4 | 1.39 | 96.27 |
| 5 | 0.77 | 98.89 |

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

That which is claimed:

1. An enantiomeric compound consisting of a structure of Formula (RS,Z-2):

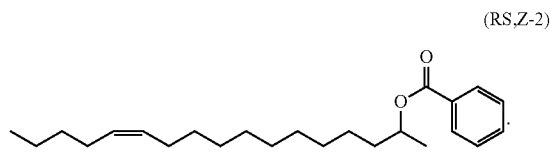

(RS,Z-2)

2. An enantiomeric compound consisting of a structure of Formula (R,Z-2):

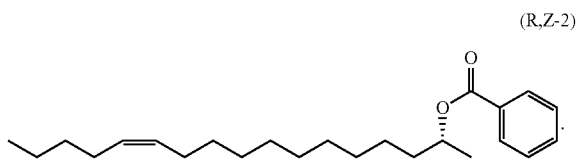 [SMILES: CCCC/C=C\CCCCCCCCC[C@@H](C)OC(=O)c1ccccc1]

(R,Z-2)

3. An enantiomeric compound consisting of a structure of Formula (S,Z-2):

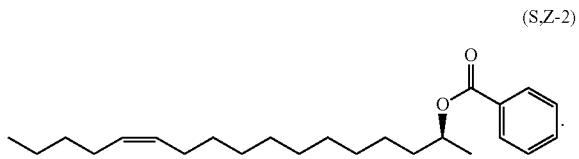 [SMILES: CCCC/C=C\CCCCCCCCC[C@H](C)OC(=O)c1ccccc1]

(S,Z-2)

* * * * *